(12) United States Patent
Hori (10) Patent No.: US 11,423,894 B2
(45) Date of Patent: Aug. 23, 2022

(54) ENCOURAGING SPEECH SYSTEM, ENCOURAGING SPEECH METHOD, AND PROGRAM

(71) Applicant: Toyota Jidosha Kabushiki Kaisha, Toyota (JP)

(72) Inventor: Tatsuro Hori, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 221 days.

(21) Appl. No.: 16/749,551

(22) Filed: Jan. 22, 2020

(65) Prior Publication Data

US 2020/0243087 A1 Jul. 30, 2020

(30) Foreign Application Priority Data

Jan. 24, 2019 (JP) .............................. JP2019-010049

(51) Int. Cl.
*G10L 15/22* (2006.01)
*G10L 15/30* (2013.01)
(Continued)

(52) U.S. Cl.
CPC ................ *G10L 15/22* (2013.01); *G06N 5/04* (2013.01); *G06N 20/00* (2019.01); *G10L 13/00* (2013.01);
(Continued)

(58) Field of Classification Search
CPC ......... G10L 13/00; G10L 15/22; G10L 15/78; G10L 15/08; G10L 17/00; G10L 25/63; G10L 15/1815; G10L 15/26; G10L 17/06; G10L 17/26; G10L 25/48; G10L 25/51; G10L 15/24; G10L 15/30; G10L 2015/227; G16H 10/60; G16H 50/20; G16H 10/20; G16H 40/67; G16H 40/63; G16H 50/50; G16H 80/00; G06F 3/04886; G06F 3/167; G06F 40/174; G06F 40/30; G06F 40/40;
(Continued)

(56) References Cited

U.S. PATENT DOCUMENTS 8,781,859 B2 * 7/2014 Manning ................ G06Q 30/01
705/2
9,536,049 B2 * 1/2017 Brown .................... G16H 50/20
(Continued)

FOREIGN PATENT DOCUMENTS

JP 2015-219583 A 12/2015
JP 2016-110331 A 6/2016
JP 2017-174339 A 9/2017

*Primary Examiner* — Vijay B Chawan
(74) *Attorney, Agent, or Firm* — Dinsmore & Shohl LLP (57) ABSTRACT

An encouraging speech system performs an encouraging speech for encouraging an action of each user for each of a plurality of users. The encouraging speech system includes: state detection means for detecting states of the respective users; information acquisition means for acquiring information that relates to nursing care or medical care of the respective users; and encouraging speech means for associating the states of the respective users detected by the state detection means with the information that relates to the nursing care or the medical care of the respective users acquired by the information acquisition means and making the encouraging speech for each of the users so as to encourage interaction between the users.

8 Claims, 5 Drawing Sheets

(51) Int. Cl.
*G10L 15/24* (2013.01)
*G06N 20/00* (2019.01)
*G06N 5/04* (2006.01)
*G16H 80/00* (2018.01)
*G16H 10/60* (2018.01)
*G10L 25/78* (2013.01)
*G10L 13/00* (2006.01)

(52) U.S. Cl.
CPC .............. *G10L 15/24* (2013.01); *G10L 15/30* (2013.01); *G10L 25/78* (2013.01); *G16H 10/60* (2018.01); *G16H 80/00* (2018.01); *G10L 2015/227* (2013.01)

(58) Field of Classification Search
CPC ........ G06N 20/00; G06N 3/004; G06N 2/006; G06N 5/002; G06N 5/04
USPC ......... 704/235, 246, 270, 270.1, 9; 705/2, 3, 705/14.53; 707/999.001, 999.107; 709/206
See application file for complete search history.

(56) References Cited

U.S. PATENT DOCUMENTS

| | | | | |
|---|---|---|---|---|
| 9,899,024 | B1* | 2/2018 | Kanevsky | G09B 19/04 |
| 10,020,007 | B2* | 7/2018 | Mizumoto | H04M 3/42221 |
| 10,304,314 | B2* | 5/2019 | Fateh | G16H 40/63 |
| 10,726,846 | B2* | 7/2020 | Vergyri | A61B 5/7282 |
| 2002/0002558 | A1* | 1/2002 | Krause | G06Q 30/02 |
| 2003/0182123 | A1* | 9/2003 | Mitsuyoshi | G10L 13/033 704/270 |
| 2005/0055242 | A1* | 3/2005 | Bello | G16H 20/17 705/2 |
| 2009/0002178 | A1* | 1/2009 | Guday | G06F 3/0346 340/573.1 |
| 2010/0278318 | A1* | 11/2010 | Flockhart | H04M 3/51 379/88.04 |
| 2010/0325218 | A1* | 12/2010 | Castro | G06Q 10/10 709/206 |
| 2014/0247155 | A1* | 9/2014 | Proud | A61B 5/1118 340/870.16 |
| 2014/0249853 | A1* | 9/2014 | Proud | G06Q 10/10 705/3 |
| 2015/0032535 | A1* | 1/2015 | Li | G06Q 30/0255 705/14.53 |
| 2015/0081299 | A1* | 3/2015 | Jasinschi | G10L 17/22 704/246 |
| 2015/0125832 | A1* | 5/2015 | Tran | G09B 19/0092 434/127 |
| 2015/0262016 | A1* | 9/2015 | Rothblatt | A61B 5/4088 348/77 |
| 2016/0307571 | A1* | 10/2016 | Mizumoto | H04L 12/1831 |
| 2017/0262604 | A1* | 9/2017 | Francois | G06Q 10/10 |
| 2017/0277268 | A1 | 9/2017 | Ono et al. | |
| 2018/0068082 | A1* | 3/2018 | Brown | G10L 15/22 |
| 2018/0330626 | A1* | 11/2018 | Donadio | G16H 50/20 |
| 2019/0051415 | A1* | 2/2019 | Owen | G16H 50/20 |
| 2019/0096395 | A1* | 3/2019 | Fujii | G10L 15/22 |
| 2019/0108841 | A1* | 4/2019 | Vergyri | G10L 17/06 |
| 2020/0242966 | A1* | 7/2020 | Hori | G10L 25/78 |

* cited by examiner

ENCOURAGING SPEECH SYSTEM, ENCOURAGING SPEECH METHOD, AND PROGRAM

CROSS REFERENCE TO RELATED APPLICATIONS

This application is based upon and claims the benefit of priority from Japanese patent application No. 2019-010049, filed on Jan. 24, 2019, the disclosure of which is incorporated herein in its entirety by reference.

BACKGROUND

The present disclosure relates to an encouraging speech system, an encouraging speech method, and a program for making a speech for encouraging a user's action.

A system for determining a topic to be provided for a user based on language information indicating an action history of the user has been known (see, for example, Japanese Unexamined Patent Application Publication No. 2015-219583).

SUMMARY

In the above system, a conversation is performed with the system by obtaining a state of one user. Therefore, there are limitations in increasing the amount of activity of each of the users.

The present disclosure has been made in order to solve the aforementioned problem, and a main object of the present disclosure is to provide an encouraging speech system, an encouraging speech method, and a program capable of efficiently increasing the amount of activity of each of the users.

One aspect of the present disclosure to accomplish the aforementioned object is an encouraging speech system for performing an encouraging speech for encouraging an action of each user for each of a plurality of users, the encouraging speech system including:

state detection means for detecting states of the respective users;

information acquisition means for acquiring information that relates to nursing care or medical care of the respective users; and encouraging speech means for associating the states of the respective users detected by the state detection means with the information that relates to the nursing care or the medical care of the respective users acquired by the information acquisition means and making the encouraging speech for each of the users so as to encourage interaction between the users.

In this aspect, the information that relates to the nursing care or the medical care of the respective users may include information indicating moving abilities of the respective users, and the encouraging speech means may associate the states of the respective users with the information on the moving abilities of the respective users, and make the encouraging speech so as to encourage interaction between the users.

In this aspect, the information that relates to the nursing care or the medical care of the respective users may include information regarding wards of the respective users, and the encouraging speech means may perform the encouraging speech so as to encourage interaction between users who stay in the same ward.

In this aspect, the information acquisition means may further acquire user profile information indicating characteristics of the respective users, and the encouraging speech means may associate the states of the respective users with information that relates to the nursing care or the medical care of the respective users acquired by the information acquisition means and the user profile information, and make the encouraging speech so as to encourage interaction between the users.

In this aspect, the user profile information may include at least one of interpersonal relation information indicating an interpersonal relation between the respective users, age, hobbies, sex, and hometown.

In this aspect, the encouraging speech means may perform an encouraging speech for encouraging interaction between the respective users when it is determined that the interpersonal relation between the respective users is good based on the interpersonal relation information of the user profile information.

In this aspect, the encouraging speech system may further include informing means for informing, when it is determined that a user for which the encouraging speech means performs the encouraging speech based on the information on the moving abilities of the respective users needs to move with assistance of a caregiver, the caregiver of the information indicating that the user needs the assistance.

One aspect of the present disclosure to accomplish the aforementioned object may be an encouraging speech method for performing an encouraging speech for encouraging an action of each user for each of a plurality of users, the encouraging speech method including the steps of:

detecting states of the respective users;

acquiring information that relates to nursing care or medical care of the respective users; and associating the states of the respective users that have been detected with the acquired information that relates to the nursing care or the medical care of the respective users and making the encouraging speech for each of the users so as to encourage interaction between the users.

One aspect of the present disclosure to accomplish the aforementioned object may be a program for performing an encouraging speech for encouraging an action of each user for each of a plurality of users, the program causing a computer to execute the following processing of:

detecting states of the respective users;

acquiring information that relates to nursing care or medical care of the respective users; and associating the states of the respective users that have been detected with the acquired information that relates to the nursing care or the medical care of the respective users and making the encouraging speech for each of the users so as to encourage interaction between the users.

According to the present disclosure, it is possible to provide an encouraging speech system, an encouraging speech method, and a program capable of efficiently increasing the amount of activity of each of the users.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

First Embodiment

Figure 1:
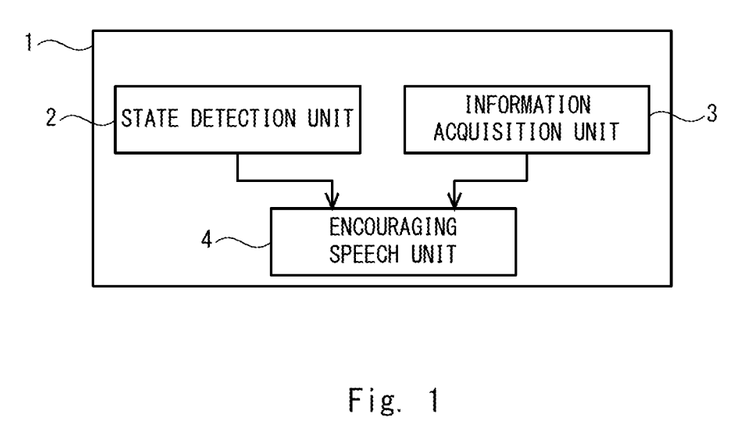
FIG. 1 is a block diagram showing a schematic system configuration of an encouraging speech system according to a first embodiment of the present disclosure.

Hereinafter, with reference to the drawings, embodiments of the present disclosure will be explained. FIG. 1 is a block diagram showing a schematic system configuration of an encouraging speech system according to a first embodiment of the present disclosure. An encouraging speech system 1 according to the first embodiment outputs an encouraging speech for encouraging an action of each user for each of the users in relation to nursing care or medical care of the user. It is therefore possible to encourage interaction between the respective users and to increase the amount of activity of each of the users.

The user is a patient who stays in a medical facility (hospital etc.), a care receiver who stays in a nursing care facility, an elderly person who lives in a nursing home, etc. The encouraging speech system 1 performs encouraging speeches so as to encourage interaction between the users, thereby increasing the amount of activity of each of the users. The encouraging speech system 1 is mounted on, for example, a robot, a Personal Computer (PC), or a mobile terminal (a smartphone, a tablet etc.), and makes a conversation with the user.

Incidentally, in the interaction system according to related art, interaction is performed with an apparatus by obtaining the state of one user. Therefore, there are limitations in increasing the amount of activity of each of the users.

On the other hand, the encouraging speech system 1 according to this first embodiment associates the states of the respective users with information that relates to nursing care or medical care of the respective users, and makes an encouraging speech to each of the users so as to encourage interaction between the users. Accordingly, it is possible to actively encourage interaction between a plurality of users, which is beyond interaction between a person and an apparatus, and efficiently increase the amount of activity of each of the users. Further, it is possible to encourage users to interact with each other appropriately in view of not only the current states of the respective users but also the information that relates to the nursing care or the medical care of the respective users. That is, it is possible to efficiently increase the amount of activity of each of the users.

The encouraging speech system 1 may be formed by, for example, hardware mainly using a microcomputer including a Central Processing Unit (CPU) that performs arithmetic processing and so on, a memory that is composed of a Read Only Memory (ROM) and a Random Access Memory (RAM) and stores an arithmetic program executed by the CPU and the like, an interface unit (I/F) that externally receives and outputs signals, and so on. The CPU, the memory, and the interface unit are connected with one another through a data bus or the like.

The encouraging speech system 1 according to this first embodiment includes a state detection unit 2 configured to detect states of the respective users, an information acquisition unit 3 configured to acquire information that relates to the nursing care or the medical care of the respective users (hereinafter this information will be referred to as nursing care medical information), and an encouraging speech unit 4 configured to perform an encouraging speech so as to encourage interaction between the users. The state detection unit 2, the information acquisition unit 3, and the encouraging speech unit 4 are interconnected by a wire or wirelessly.

The state detection unit 2 is one specific example of state detection means. The state detection unit 2 is provided in each of the rooms of the users, etc. The state detection unit 2 may be mounted on, for example, an interaction robot, an artificial intelligence (AI) speaker or the like installed in each of the rooms of the users.

The state detection unit 2 detects the current state of the user such as a state in which each user is sleeping, a state in which each user is awake, a state in which each user is busy (a state in which each user meets a visitor), a state in which each user has free time, etc. The state detection unit 2 detects the current state of the user using a camera, a microphone, or a Kinect sensor. The state detection unit 2 is able to perform, for example, pattern matching processing on each user's image captured by a camera, thereby detecting the user's state.

The state detection unit 2 may learn the states of the respective users using a neural network or the like, and detect the states of the respective users using the results of the learning. For example, a user who has free time corresponds to a user who does nothing (a state in which the user does not move continuously for equal to or more than a predetermined period of time) in a state in which this user is awake (the eyes are opened). The state detection unit 2 outputs the user's state that has been detected to the information acquisition unit 3 and the encouraging speech unit 4.

The information acquisition unit 3 is one specific example of information acquisition means. The information acquisition unit 3 acquires nursing care medical information of the respective users. The nursing care medical information of the respective users includes, for example, information indicating moving abilities of the respective users such as users who are unable to move (bedridden state), users who can walk, users who can walk with a stick, users who can move using a wheelchair, users who can move with assistance by a caregiver (hereinafter this state will be referred to as a "movement with assistance"). Further, the nursing care medical information of the respective users includes information regarding the type of the ward the respective users stay (a general ward, a care ward, etc.).

The information acquisition unit 3 may calculate the nursing care medical information of the respective users by performing pattern matching processing or the like on user's images obtained from the state detection unit 2. The information acquisition unit 3 may calculate the nursing care medical information of the respective users based on table information in which the nursing care medical information of the respective users is associated with the respective users. The information acquisition unit 3 may specify, for example, the users based on the user's images obtained from the state detection unit 2 and acquire the nursing care medical information of the user specified from the table information. The table information may be set in the information acquisition unit 3 in advance. Further, the information acquisition unit 3 may learn the nursing care medical information of the respective users using a neural network or the like and detect the nursing care medical information of the respective users using the results of the learning. The information acquisition unit 3 outputs the acquired nursing care medical information of the respective users to the encouraging speech unit 4.

The encouraging speech unit 4 is one specific example of encouraging speech means. The encouraging speech unit 4 associates the states of the respective users detected by the state detection unit 2 with the nursing care medical information of the respective users acquired by the information acquisition unit 3 and makes an encouraging speech to each of the users in order to encourage interaction between the respective users.

Figure 2:
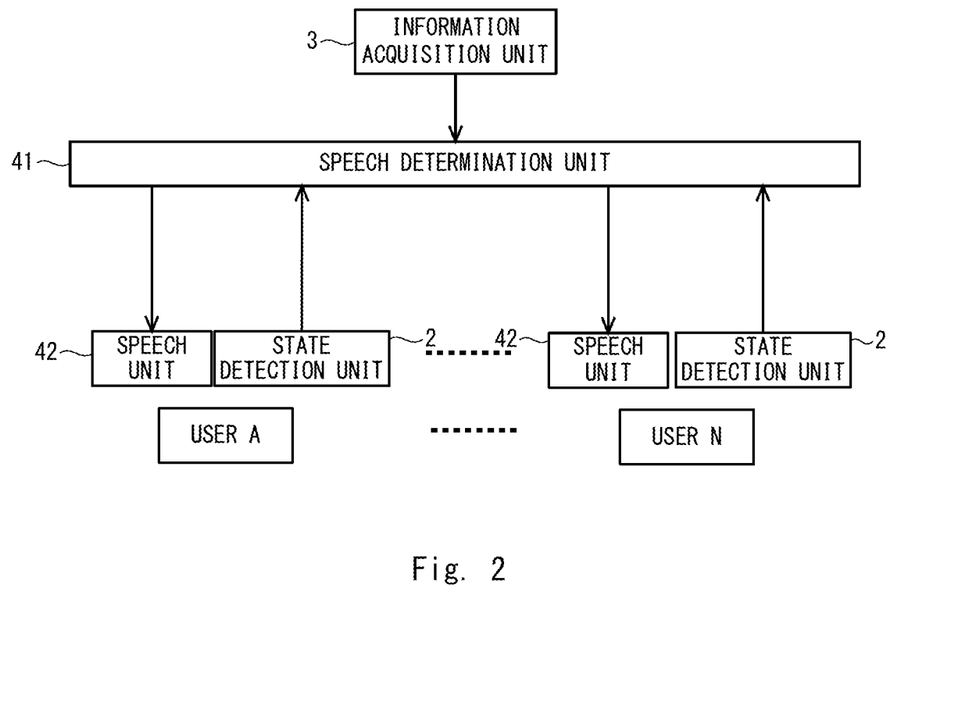
FIG. 2 is a block diagram showing a schematic configuration of an encouraging speech unit.

FIG. 2 is a block diagram showing a schematic configuration of the encouraging speech unit. The encouraging speech unit 4 includes a speech determination unit 41 configured to select users who are to be encouraged to interact with each other and determine the content of the encouraging speech to be made to each of the users, and a speech unit 42 configured to make a speech in accordance with the determination.

The aforementioned information acquisition unit 3 and speech determination unit 41 may be provided in an external server or the like. The state detection unit 2, the information acquisition unit 3, the speech determination unit 41, and the speech unit 42 may be interconnected via a network.

The speech unit 42 is formed, for example, as a speaker such as an AI speaker. The speech unit 42 is provided in each of the rooms of the users. The speech unit 42 may be provided, for example, in an interaction robot installed in the room of each of the users. The speech unit 42 and the state detection unit 2 may be integrally formed. The speech unit 42 and the user in each room are associated with each other in advance, and are set in the speech determination unit 41. The speech determination unit 41 may specify each user based on each user's images obtained from the state detection unit 2 and associate the user and the speech unit 42.

The speech determination unit 41 outputs a command signal to the speech unit 42 so as to make a speech including the determined content of the encouraging speech for the speech unit 42 associated with the user. The speech unit 42 outputs the voice of the encouraging speech to each user in accordance with the command signal output from the speech determination unit 41.

The speech determination unit 41 determines two or more users to be encouraged to interact with each other from among the plurality of users based on the states of the respective users detected by the state detection unit 2, the nursing care medical information of the respective users acquired by the information acquisition unit 3, and the combination information. In the combination information, a combination of users when the respective users are encouraged to interact with each other is set regarding the states of the respective users and the nursing care medical information of the respective users.

For example, information indicating that users who are awake should be combined, and information indicating that users who are sleeping should not be combined are set in the combination information. Information indicating that users who have free time should be combined is set, and information indicating that users who are busy should not be combined are set in the combination information. Information indicating that users who stay in the same ward should be combined is set in the combination information.

The speech determination unit 41 determines, based on the combination information, a user A who stays awake and a user B who stays awake to be the users who are to be encouraged to interact with each other. The speech determination unit 41 determines, based on the combination information, the user A who has free time, the user B who has free time, and a user C who has free time to be the users who are to be encouraged to interact with one another. The speech determination unit 41 determines, based on the combination information, the user A who is in the general ward and has free time, the user B who is in the general ward and has free time, and the user C who is in the general ward and has free time to be the users who are to be encouraged to interact with one another.

As stated above, by actively encouraging interaction between users who stay awake, users who have free time, or users who stay in a ward of the same type, it is possible to efficiently increase the amount of activity of each of the users. The combination information is set in the speech determination unit 41 in advance. The setting of the combination information can be arbitrarily changed by the user via an input apparatus or the like.

Next, the speech determination unit 41 determines the contents of speeches to be output to the respective users who are to be encouraged to interact with each other based on the nursing care medical information of the respective users. The speech determination unit 41 may determine the contents of speeches to be output to the respective users who are to be encouraged to interact with each other based on the information indicating the moving abilities of the respective users.

For example, the speech determination unit 41 determines the content of the encouraging speech so as to cause a user who has a high moving ability to move to a place where a user who has a moving ability lower than that of the above user is present. Users who can normally walk have the highest moving ability, followed by users who can walk using a stick, then by users who can move using a wheelchair, and users who cannot move have the lowest moving ability.

Therefore, the speech determination unit 41 may determine the content of the encouraging speech so as to cause the user A who has a high moving ability and can walk to a place where the user B who has a low moving ability and is in a wheelchair is present based on the nursing care medical information of the respective users.

More specifically, the speech determination unit 41 determines the content of the encouraging speech "Why don't you go to see the user B?" to be output to the user A. The speech unit 42 associated with the user A outputs the voice "Why don't you go to see the user B?" to the user A in accordance with the content of the encouraging speech determined by the speech determination unit 41.

On the other hand, the speech determination unit 41 determines the content of the encouraging speech "The user A will come here to talk to you shortly." to be output to the user B. The speech unit 42 associated with the user B outputs the voice "The user A will come here to talk to you shortly." to the user B in accordance with the content of the encouraging speech determined by the speech determination unit 41.

The speech determination unit 41 may determine the content of the encouraging speech so as to let the users move to a predetermined place (a resting place, a common space, a restaurant, a cafe, etc.) within a range in which the users who will interact with each other can move based on the nursing care medical information of the respective users. The predetermined place may be set in the speech determination unit 41 in advance.

When, for example, the users A and B can move using a wheelchair, the range in which the users A and B can move is limited to a resting place or the like which is relatively near. The speech determination unit 41 determines the contents of the encouraging speeches to let the users A and B move to the resting place based on the nursing care medical information of the respective users.

More specifically, the speech determination unit 41 determines the content of the encouraging speech "Why don't you go to the resting place? B is there." to be output to the user A. On the other hand, the speech determination unit 41 determines the content of the encouraging speech "Why don't you go to the resting place? A is there." to be output to the user B. As stated above, by performing encouraging speeches so as to encourage interaction among the users in view of the moving abilities of the respective users, it is possible to efficiently increase the amount of activity of each of the users.

The state detection unit 2 may detect a user's reaction in response to the encouraging speech made by the speech unit 42. The speech determination unit 41 may change the combination information based on the user's reaction in response to the encouraging speech detected by the state detection unit 2. When, for example, a user has not acted although an encouraging speech was made based on an image indicating the user's reaction in response to the encouraging speech, the speech determination unit 41 performs change so as to exclude the combination including this user in the combination information. Accordingly, it is possible to encourage the interaction between the users more efficiently in view of the user's reaction in response to the encouraging speech.

Figure 3:
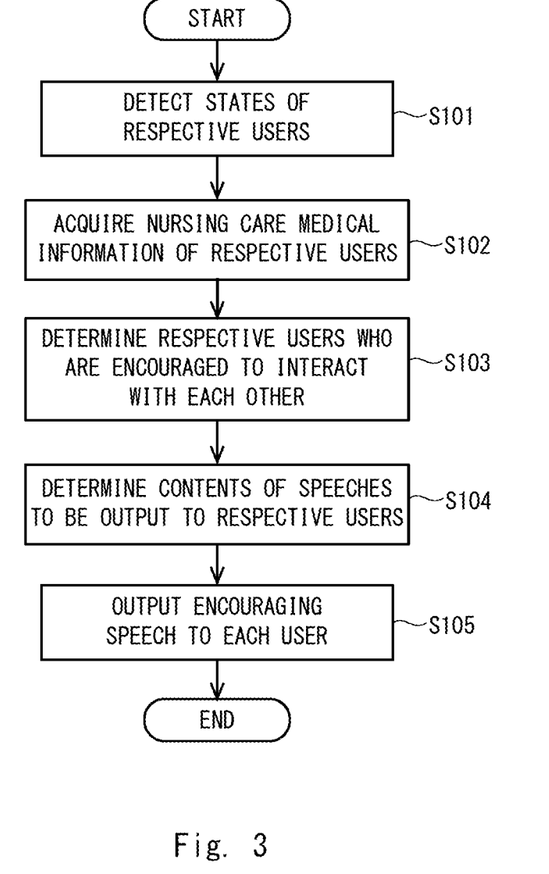
FIG. 3 is a flowchart showing a flow of an encouraging speech method according to the first embodiment of the present disclosure.

Next, a flow of the encouraging speech method according to the first embodiment will be explained in detail. FIG. 3 is a flowchart showing the flow of the encouraging speech method according to the first embodiment.

The state detection unit 2 detects the current states of the users using a camera or the like and outputs the states of the users that have been detected to the information acquisition unit 3 and the encouraging speech unit 4 (Step S101).

The information acquisition unit 3 acquires the nursing care medical information of the respective users based on the user's images obtained from the state detection unit 2, and outputs the acquired nursing care medical information of the respective users to the encouraging speech unit 4 (Step S102).

The speech determination unit 41 of the encouraging speech unit 4 determines two or more users who are encouraged to interact with each other from among the plurality of users based on the states of the respective users detected by the state detection unit 2, the nursing care medical information of the respective users acquired by the information acquisition unit 3, and the combination information (Step S103).

The speech determination unit 41 determines the contents of speeches to be output to the respective users that have been determined to be encouraged to interact with each other based on the nursing care medical information of the respective users (Step S104).

The speech determination unit 41 outputs a command signal to the speech unit 42 so as to make a speech including the determined content of the encouraging speech for the speech unit 42 that corresponds to the determined user. The speech unit 42 outputs the voice of the encouraging speech to each user in accordance with the command signal from the speech determination unit 41 (Step S105).

As described above, the encouraging speech system 1 according to the first embodiment associates the states of the respective users detected by the state detection unit 2 with the information that relates to the nursing care or the medical care of the respective users acquired by the information acquisition unit 3, and makes an encouraging speech for each of the users so as to encourage interaction between the users. It is therefore possible to efficiently increase the amount of activity of the user.

Second Embodiment

In a second embodiment of the present disclosure, the information acquisition unit 3 further acquires user profile information indicating characteristics of the respective users. The encouraging speech unit 4 associates the states of the respective users detected by the state detection unit 2 with the nursing care medical information of the respective users acquired by the information acquisition unit 3 and the user profile information, and performs an encouraging speech so as to encourage interaction between the users. Accordingly, it is possible to encourage interaction between the users more appropriately in view of, besides the current states of the respective users and the nursing care medical information of the respective users, the user profile information. That is, it is possible to increase the amount of activity of each of the users more efficiently.

The user profile information includes at least one of interpersonal relation information indicating an interpersonal relation between the respective users, age, hobbies, sex, and hometown. The interpersonal relation information is, for example, information indicating whether the interpersonal relation between the respective users is good or not.

The information acquisition unit 3 may calculate the user profile information of each of the users based on the table information in which the user profile information of the respective users is associated with the respective users in advance. For example, the information acquisition unit 3 may specify each of the users based on user's images from the state detection unit 2 and acquire the user profile information of each of the users from the table information. The table information may be set in the information acquisition unit 3 in advance.

The speech determination unit 41 of the encouraging speech unit 4 determines two or more users who are to be encouraged to interact with each other from among the plurality of users based on the states of the respective users detected by the state detection unit 2, the interpersonal relation information of each user profile information acquired by the information acquisition unit 3, and the combination information.

Besides the aforementioned combination information, information indicating that users with good interpersonal relations should be combined with each other, information indicating that users with bad interpersonal relations should not be combined with each other, and the like may be set as the combination information. The interpersonal relation information includes information indicating the interpersonal relation between the respective users such as, for example, information indicating that the interpersonal relation between the user A and the user B is good or information indicating that the interpersonal relation between the user C and the user D is bad. The encouraging speech unit 4 performs an encouraging speech for encouraging interaction between users with good interpersonal relations based on the interpersonal relation information and the combination information. It is therefore possible to encourage the interaction between the respective users more smoothly, and to efficiently increase the amount of activity of each of the users.

Besides the combination information of the interpersonal relation stated above, information indicating that users with the same age group, the same hobbies, the same sex, and the same hometown should be combined with each other may be set in the combination information.

The speech determination unit 41 determines, for example, the user A and the user B who are on good terms with each other to be the users who are to be encouraged to interact with each other based on the states of the respective users, the interpersonal relation information of each user profile information, and the combination information. On the other hand, the speech determination unit 41 does not determine the user C and the user D who are on bad terms with each other to be the users who are to be encouraged to interact with each other based on the states of the respective users, the interpersonal relation information of each user profile information, and the combination information. The speech determination unit 41 determines the user A and the user B who are on good terms with each other and stay in the same ward to be the users who are to be encouraged to interact with each other based on the states of the respective users, the nursing care medical information of the respective users, the interpersonal relation information of each user profile information, and the combination information.

As stated above, interaction between the respective users can be encouraged more smoothly in view of not only the current states of the respective users and the nursing care medical information of the respective users but also the user profile information such as the interpersonal relation and the type of the ward, and the amount of activity of each of the users can be increased more efficiently.

Third Embodiment

Figure 4:
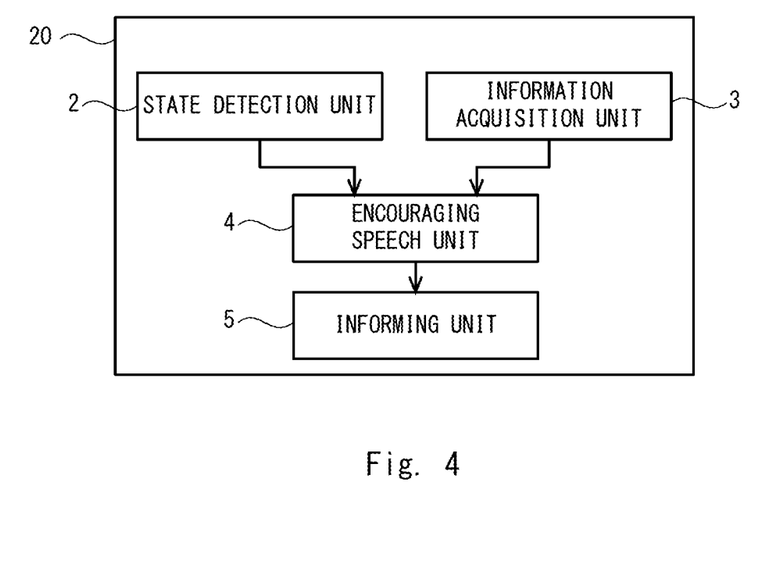
FIG. 4 is a block diagram showing a schematic system configuration of an encouraging speech system according to a third embodiment of the present disclosure.

FIG. 4 is a block diagram showing a schematic system configuration of an encouraging speech system 20 according to a third embodiment of the present disclosure. In the third embodiment of the present disclosure, when the speech determination unit 41 has determined that a user who is to be encouraged to interact with others needs assistance (corresponds to "movement with assistance") based on the nursing care medical information of the respective users, the informing unit 5 informs the caregiver of information indicating that the user needs assistance. Therefore, the user who needs assistance is able to automatically call for the caregiver, move with assistance by the caregiver, and actively interact with other users. It is therefore possible to efficiently increase the amount of activity of the user.

The speech determination unit 41 determines the users who are to be encouraged to interact with each other from among the plurality of users based on the states of the respective users detected by the state detection unit 2, the nursing care medical information of the respective users acquired by the information acquisition unit 3, and the combination information.

When the speech determination unit 41 has determined that each user that has been determined corresponds to "movement with assistance" based on the nursing care medical information of the respective users, the speech determination unit 41 transmits an information signal indicating that the user needs assistance to the informing unit 5 in order to inform the caregiver that the user needs assistance. The informing unit 5 is one specific example of informing means. The informing unit 5 sends, for example, information such as "The user A is calling you." to the caregiver in response to the information signal from the speech determination unit 41. The communication between the speech determination unit and the informing unit 5 is connected to each other by a wire or wirelessly. The informing unit 5 is formed of a speaker that outputs a voice, a display that performs display, etc. The informing unit 5 is provided, for example, in a waiting room where the caregiver is on duty at all times.

The speech determination unit 41 determines, for example, the users A and B to be the users who are to be encouraged to interact with each other based on the states of the respective users detected by the state detection unit 2, the nursing care medical information of the respective users acquired by the information acquisition unit 3, and the combination information.

The speech determination unit 41 determines the contents of the encouraging speeches to cause the users A and B to move to a shared space within the range in which the users A and B can move based on the nursing care medical information of the users A and B. The speech unit 42 associated with the user A outputs the voice "Why don't you talk to the user B in the shared space?" to the user A in accordance with the content of the encouraging speech made by the speech determination unit 41. On the other hand, the speech unit 42 associated with the user B outputs the voice "Why don't you talk to the user A in the shared space?" to the user B in accordance with the content of the encouraging speech made by the speech determination unit 41.

At the same time, when the speech determination unit 41 has determined that the determined users A and B correspond to "movement with assistance" based on the nursing care medical information of the respective users, the speech determination unit 41 transmits an information signal for informing the caregiver of information indicating that the users need assistance to the informing unit 5. The informing unit 5 sends information such as "The users A and B need your assistance." to the caregiver in response to the information signal from the speech determination unit 41. As described above, the users A and B who need assistance are able to automatically call for the caregiver, move to the shared space by the assistance provided by the caregiver, and actively interact with each other. It is therefore possible to increase the amount of activity of each of the users A and B more efficiently.

Figure 5:
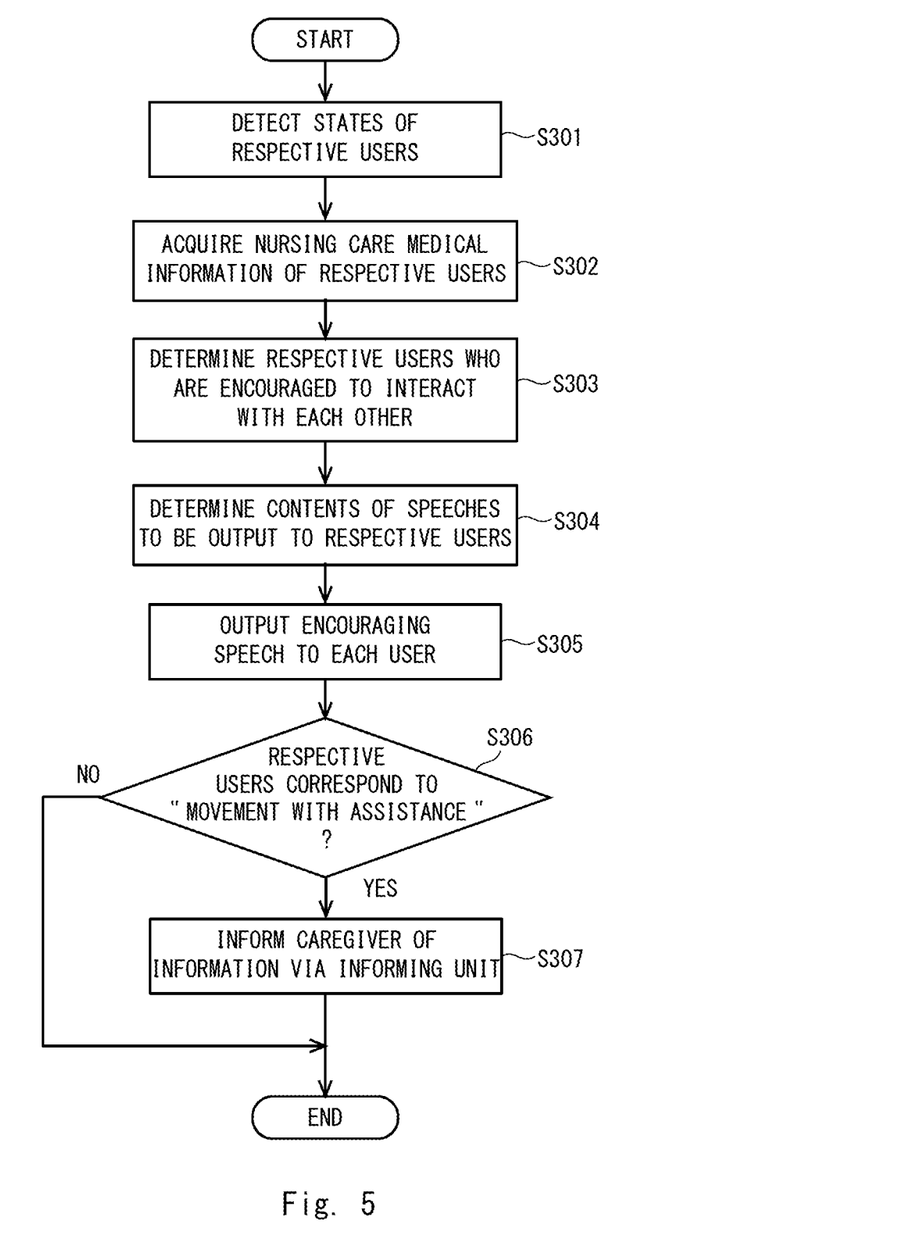
FIG. 5 is a flowchart showing a flow of an encouraging speech method according to the third embodiment of the present disclosure.

Next, a flow of the encouraging speech method according to the third embodiment will be explained in detail. FIG. 5 is a flowchart showing the flow of the encouraging speech method according to the third embodiment.

The state detection unit 2 detects the current states of the users using a camera or the like, and outputs the states of the users that have been detected to the information acquisition unit 3 and the encouraging speech unit 4 (Step S301).

The information acquisition unit 3 acquires the nursing care medical information of the respective users based on the user's images obtained from the state detection unit 2 and outputs the acquired nursing care medical information of the respective users to the encouraging speech unit 4 (Step S302).

The speech determination unit 41 of the encouraging speech unit 4 determines the users who are to be encouraged to interact with each other from among the plurality of users based on the states of the respective users detected by the state detection unit 2, the nursing care medical information of the respective users acquired by the information acquisition unit 3, and the combination information (Step S303).

The speech determination unit 41 determines the contents of speeches to be output to the respective users that have been determined to be encouraged to interact with each other based on the nursing care medical information of the respective users (Step S304).

The speech determination unit 41 outputs a command signal to the speech unit 42 so as to make a speech including the determined content of the encouraging speech for the speech unit 42 that corresponds to the determined user. The speech unit 42 outputs the voice of the encouraging speech to each user in accordance with the command signal from the speech determination unit 41 (Step S305).

The speech determination unit 41 determines whether the respective users that have been determined correspond to "movement with assistance" based on the nursing care medical information of the respective users (Step S306). When the speech determination unit 41 has determined that the respective users that have been determined correspond to "movement with assistance" (YES in Step S306), the speech determination unit 41 informs the caregiver of information indicating that the user needs assistance via the informing unit 5 (Step S307). On the other hand, when the speech determination unit 41 has determined that the respective users that have been determined do not correspond to "movement with assistance" (NO in Step S306), this processing is ended.

Note that the above processing from (Step S306) to (Step S307) may be executed before the above processing from (Step S304) to (Step S305) or the above processing from (Step S306) to (Step S307) and the above processing from (Step S304) to (Step S305) may be concurrently executed.

While some embodiments of this disclosure have been described above, these embodiments are presented as examples and not intended to limit the scope of the disclosure. These novel embodiments can be implemented in other various forms, and various types of omissions, substitutions, or changes can be made without departing from the spirit of the disclosure. These embodiments and their modifications, as would fall within the scope and spirit of the disclosure, are included in the disclosure provided in the claims and the scope of equivalents thereof.

The present disclosure is able to achieve, for example, the processing shown in FIGS. 3 and 5 by causing a CPU to execute a computer program.

The program(s) can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g., magneto-optical disks), Compact Disc Read Only Memory (CD-ROM), CD-R, CD-R/W, and semiconductor memories (such as mask ROM, Programmable ROM (PROM), Erasable PROM (EPROM), flash ROM, Random Access Memory (RAM), etc.).

The program(s) may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A system for performing an encouraging speech for encouraging an action of each user for each of a plurality of users, the system comprising a CPU configured to:
   detect states of the respective users;
   acquire information that relates to nursing care or medical care of the respective users, the information indicating moving abilities of the respective users; and
   associate the states of the respective users with the moving abilities of the respective users and output a voice of the encouraging speech for each of the users so as to encourage interaction between the users.

2. The system according to claim 1, wherein:
   the information that relates to the nursing care or the medical care of the respective users includes information regarding wards of the respective users, and
   the CPU outputs the voice of the encouraging speech so as to encourage interaction between users who stay in the same ward.

3. The system according to claim 1, wherein the CPU is further configured to:
   acquire user profile information indicating characteristics of the respective users, and
   associate the states of the respective users with information that relates to the nursing care or the medical care of the respective users and the user profile information, and output the voice of the encouraging speech so as to encourage interaction between the users.

4. The system according to claim 3, wherein the user profile information comprises at least one of interpersonal relation information indicating an interpersonal relation between the respective users, age, hobbies, sex, and hometown.

5. The system according to claim 4, wherein the CPU is further configured to output the voice of the encouraging speech for encouraging interaction between the respective users when it is determined that the interpersonal relation between the respective users is good based on the interpersonal relation information of the user profile information.

6. The encouraging speech system according to claim 1, wherein the CPU is further configured to inform, when it is determined that a user for which the CPU outputs the voice of the encouraging speech based on the information on the moving abilities of the respective users needs to move with assistance of a caregiver, the caregiver of the information indicating that the user needs the assistance.

7. A method for performing an encouraging speech for encouraging an action of each user for each of a plurality of users, the encouraging speech method comprising the steps of:
   detecting states of the respective users;
   acquiring information that relates to nursing care or medical care of the respective users the information indicating moving abilities of the respective users; and
   associating the states of the respective users that have been detected with the moving abilities of the respective users and outputting a voice of the encouraging speech for each of the users so as to encourage interaction between the users.

8. A non-transitory computer readable medium storing a program for performing an encouraging speech for encouraging an action of each user for each of a plurality of users, the program causing a computer to execute the following processing of:

detecting states of the respective users;
acquiring information that relates to nursing care or medical care of the respective users the information indicating moving abilities of the respective users; and
associating the states of the respective users that have been detected with the moving abilities of the respective users and outputting a voice of the encouraging speech for each of the users so as to encourage interaction between the users.

* * * * *